(12) United States Patent
Liu

(10) Patent No.: US 11,071,322 B2
(45) Date of Patent: Jul. 27, 2021

(54) VAPORIZER

(71) Applicant: Tuanfang Liu, Shenzhen (CN)

(72) Inventor: Tuanfang Liu, Shenzhen (CN)

( * ) Notice: Subject to any disclaimer, the term of this patent is extended or adjusted under 35 U.S.C. 154(b) by 70 days.

(21) Appl. No.: 16/691,641

(22) Filed: Nov. 22, 2019

(65) Prior Publication Data

US 2020/0359701 A1 Nov. 19, 2020

(30) Foreign Application Priority Data

May 13, 2019 (CN) .......................... 201910395120.9
May 13, 2019 (CN) .......................... 201920694195.2

(51) Int. Cl.
*A24F 47/00* (2020.01)
*A24F 40/40* (2020.01)
*A24F 40/20* (2020.01)
*A24F 40/465* (2020.01)
*A61M 15/00* (2006.01)

(52) U.S. Cl.
CPC ......... *A24F 40/20* (2020.01); *A61M 15/0006* (2014.02); *A61M 15/0021* (2014.02)

(58) Field of Classification Search
CPC ...... A24F 47/00; A24F 47/004; A24F 47/008; A61M 15/06; A61M 15/0021
See application file for complete search history.

(56) References Cited

U.S. PATENT DOCUMENTS

| | | | |
|---|---|---|---|
| 2014/0209106 A1* | 7/2014 | Liu | A24F 40/40 131/329 |
| 2015/0013696 A1* | 1/2015 | Plojoux | A61M 15/06 131/328 |
| 2017/0013881 A1* | 1/2017 | Liu | H05B 3/12 |
| 2017/0224023 A1* | 8/2017 | Lin | A24F 40/40 |
| 2017/0245547 A1* | 8/2017 | Lipowicz | A61M 15/0081 |
| 2017/0301898 A1* | 10/2017 | Lin | A24F 40/51 |
| 2018/0049471 A1* | 2/2018 | Holoubek | A24F 40/465 |
| 2018/0279682 A1* | 10/2018 | Guo | H05B 3/44 |

* cited by examiner

*Primary Examiner* — Alex B Efta
(74) *Attorney, Agent, or Firm* — Matthias Scholl P.C.; Matthias Scholl

(57) ABSTRACT

A vaporizer, including: an eye ring; a ring comprising stainless iron; a first lock block; a first end support; a thermal insulation cotton; a stainless-steel tube; a second end support; a support cylinder; a second lock block; a magnet; a thermistor; a mounting seat; a spring support; a spring; a pneumatic switch; a silicone sleeve sleeving the pneumatic switch; annular sleeve; a coil support; an inductor; a printed circuit board; a first end cover; a first cover plate covering the first end cover; a button; a circuit board; two electrical contacts; a battery; a housing; a second end cover; a second cover plate covering the second end cover. The thermal insulation cotton is sheathed on the stainless-steel tube. The first end support and the second end support are disposed on two ends of the stainless-steel tube, respectively. The first lock block is disposed on the first end support.

1 Claim, 3 Drawing Sheets

VAPORIZER

CROSS-REFERENCE TO RELAYED APPLICATIONS

Pursuant to 35 U.S.C. § 119 and the Paris Convention Treaty, this application claims foreign priority to Chinese Patent Application No. 201910395120.9 filed May 13, 2019, and to Chinese Patent Application No. 201920694195.2 filed May 13, 2019. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to a vaporizer.

A vaporizer, colloquially known as a vape, is a device used to vaporize substances such as tobacco for inhalation.

SUMMARY

The disclosure provides a vaporizer.

The vaporizer comprises an eye ring; a ring comprising stainless iron; a first lock block; a first end support; a thermal insulation cotton; a stainless-steel tube; a second end support; a support cylinder; a second lock block; a magnet; a thermistor; a mounting seat; a spring support; a spring; a pneumatic switch; a silicone sleeve sleeving the pneumatic switch; annular sleeve; a coil support; an inductor; a printed circuit board; a first end cover; a first cover plate covering the first end cover; a button; a circuit board; two electrical contacts; a battery; a housing; a second end cover; a second cover plate covering the second end cover.

The thermal insulation cotton is sheathed on the stainless-steel tube; the first end support and the second end support are disposed on two ends of the stainless-steel tube, respectively; the first lock block is disposed on the first end support; the ring comprising stainless iron is in threaded connection to the first lock block, and the eye ring is removably disposed on the ring comprising stainless iron; the eye ring, the ring comprising stainless iron, the first lock block, and the first end support and the stainless-steel tube each comprise a central hole, so that a cigarette passes through the central hole of each component to enter the stainless-steel tube; the first end support, the stainless-steel tube, and the second end support are disposed sequentially in that order in the support cylinder; the magnet is fixed on the second lock block, and the support cylinder is supported by the second lock block; the spring is disposed in the spring support; the thermistor is disposed in the mounting seat; the mounting seat is disposed on the spring support; and the spring support is embedded in the support cylinder; the pneumatic switch is disposed in the silicone sleeve; the silicone sleeve is disposed in the annular sleeve; the annular sleeve is embedded in the coil support; the inductor is disposed on the coil support; the inductor comprises two pins and the printed circuit board is directly connected to the two pins; the coil support is disposed in the housing; the support cylinder is disposed in the coil support; the battery is disposed in the housing; the button is disposed on the housing; the two electrical contacts are directly connected to the circuit board; the two electrical contacts and the circuit board are disposed in the housing; the first cover plate and the first end cover are sequentially disposed on one end of the housing; and the second cover plate and the first end cover are sequentially disposed on the other end of the housing.

DETAILED DESCRIPTION

Figure 1:
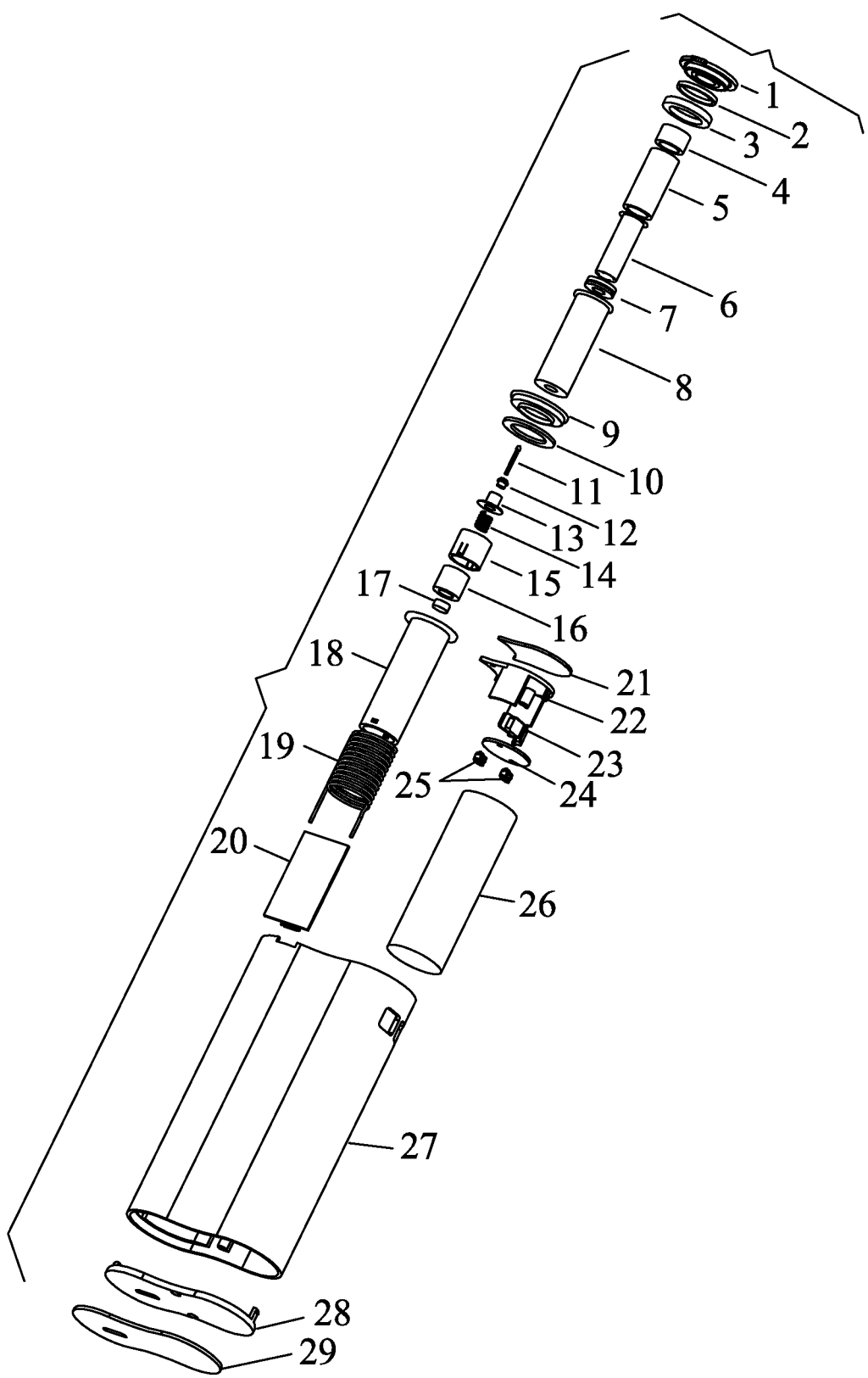
FIG. 1 is an exploded view of a vaporizer according to one embodiment of the disclosure.
Figure 2:
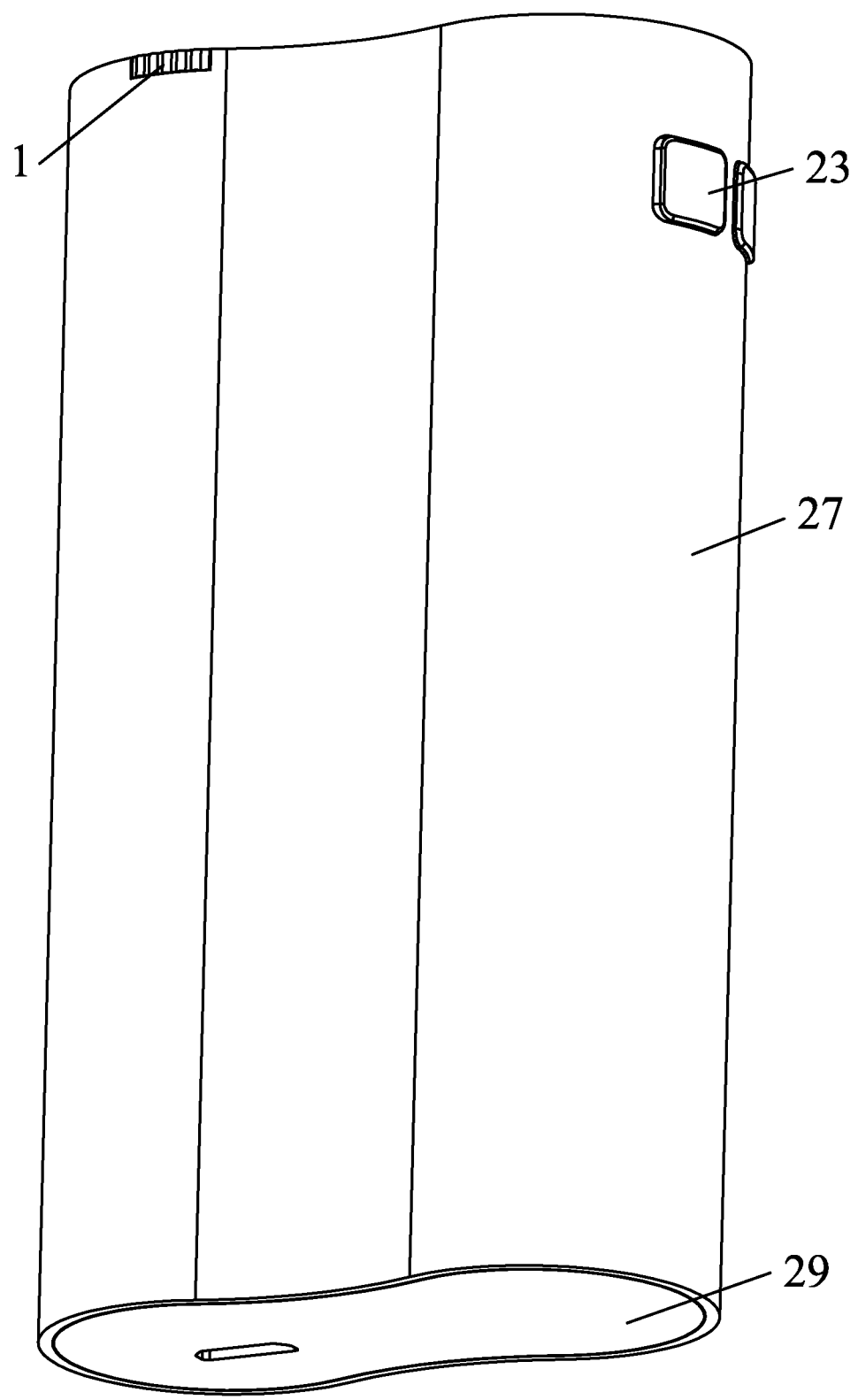
FIG. 2 is a schematic diagram of a vaporizer according to one embodiment of the disclosure.
Figure 3:
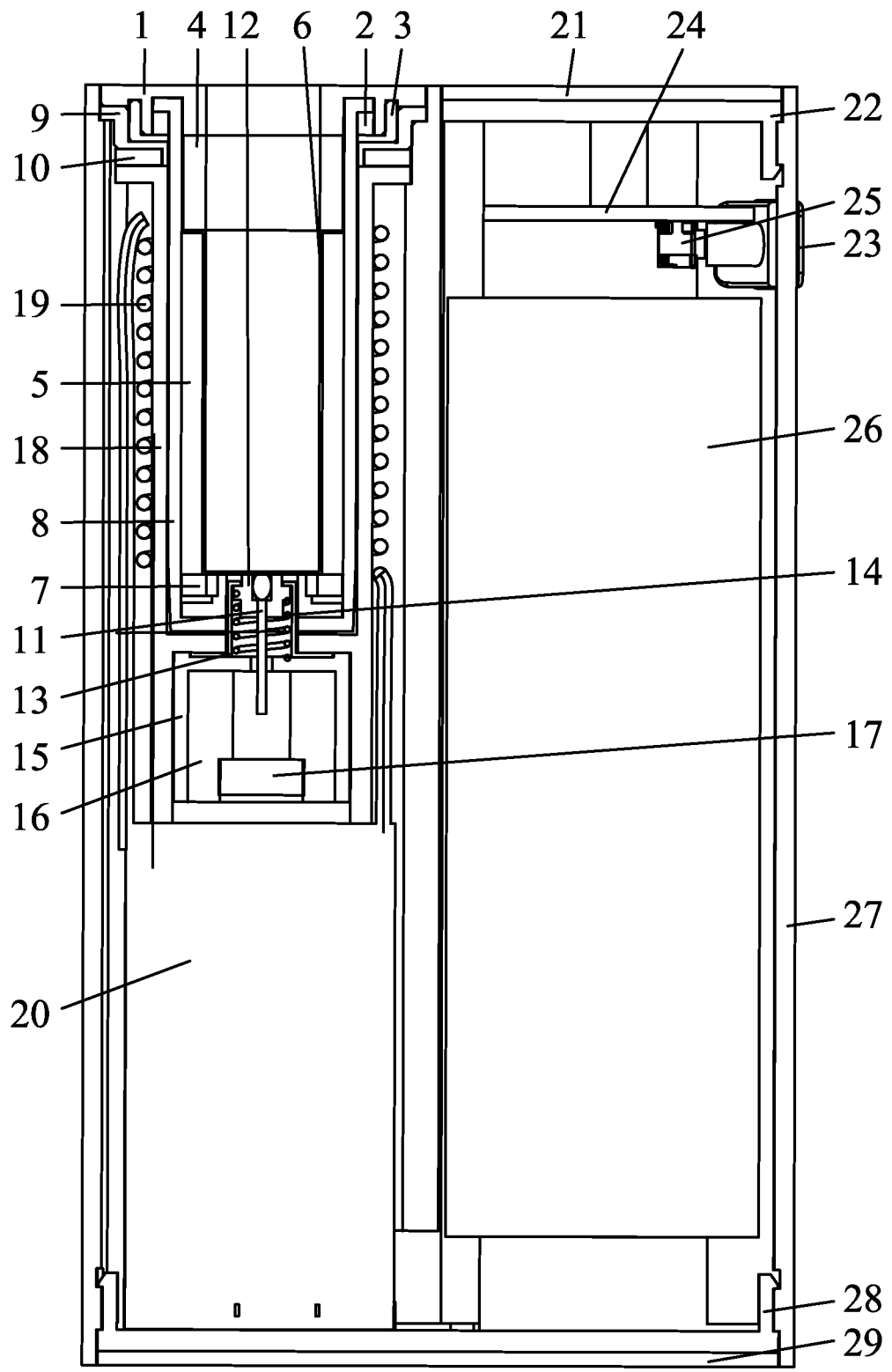
FIG. 3 is a sectional view of a vaporizer according to one embodiment of the disclosure.

To further illustrate, embodiments detailing a vaporizer are described below. It should be noted that the following embodiments are intended to describe and not to limit the disclosure.

A vaporizer comprises an eye ring 1; a ring comprising stainless iron 2; a first lock block 3; a first end support 4; a thermal insulation cotton 5; a stainless-steel tube 6; a second end support 7; a support cylinder 8; a second lock block 9; a magnet 10; a thermistor 11; a mounting seat 12; a spring support 13; a spring 14; a pneumatic switch 17; a silicone sleeve 16 sleeving the pneumatic switch 17; annular sleeve 15; a coil support 18; an inductor 19; a printed circuit board 20; a first end cover 22; a first cover plate 21 covering the first end cover 22; a button 23; a circuit board 24; two electrical contacts 25; a battery 26; a housing 27; a second end cover 28; a second cover plate 29 covering the second end cover 28.

The thermal insulation cotton 5 is sheathed on the stainless-steel tube 6; the first end support 4 and the second end support 7 are disposed on two ends of the stainless-steel tube 6, respectively; the first lock block 3 is disposed on the first end support 4; the ring comprising stainless iron 2 is in threaded connection to the first lock block 3, and the eye ring 1 is removably disposed on the ring comprising stainless iron 2; the eye ring 1, the ring comprising stainless iron 2, the first lock block 3, and the first end support 4 and the stainless-steel tube 6 each comprise a central hole, and a cigarette passes through the central hole to enter the stainless-steel tube 6; the first end support 4, the stainless-steel tube 6, and the second end support 7 are disposed sequentially in that order in the support cylinder 8; the magnet 10 is fixed on the second lock block 9, and the support cylinder 8 is supported by the second lock block 9; the spring 14 is disposed in the spring support 13; the thermistor 11 is disposed in the mounting seat 12; the mounting seat 12 is disposed on the spring support 13; and the spring support 13 is embedded in the support cylinder 8; the pneumatic switch 17 is disposed in the silicone sleeve 16; the silicone sleeve 16 is disposed in the annular sleeve 15; the annular sleeve 15 is embedded in the coil support 18; the inductor 19 is disposed on the coil support 18; the inductor 19 comprises two pins and the printed circuit board 20 is directly connected to the two pins; the coil support 18 is disposed in the housing 27; the support cylinder 8 is disposed in the coil support 18; the battery 26 is disposed in the housing 27; the button 23 is disposed on the housing 27; the two electrical contacts 25 are directly connected to the circuit board 24; the two electrical contacts 25 and the circuit board 24 are disposed in the housing 27; the first cover plate 21 and the first end cover 22 are sequentially disposed on one end of the housing 27; and the second cover plate 29 and the first end cover 28 are sequentially disposed on the other end of the housing 27.

In use, a cigarette can be inserted into the stainless-steel tube via the central holes of the eye ring, the ring comprising stainless iron, the first lock block, and the first end support. Pulling out the eye ring can separate the cigarette from the vaporizer. Press the power button of the vaporizer, the current flows through the inductor and an induced magnetic field is produced. In the induction magnetic field, due to the electromagnetic induction effect, the stainless-steel tube is automatically heated. Thus, the harmful substances of the cigarette are volatilized and degraded under the high temperature heating effect in the stainless-steel tube.

It will be obvious to those skilled in the art that changes and modifications may be made, and therefore, the aim in the appended claims is to cover all such changes and modifications.

What is claimed is:

1. A device, comprising:
   1) an eye ring;
   2) a ring comprising stainless iron;
   3) a first lock block;
   4) a first end support;
   5) a thermal insulation cotton;
   6) a stainless-steel tube;
   7) a second end support;
   8) a support cylinder;
   9) a second lock block;
   10) a magnet;
   11) a thermistor;
   12) a mounting seat;
   13) a spring support;
   14) a spring;
   15) a pneumatic switch;
   16) a silicone sleeve sleeving the pneumatic switch;
   17) an annular sleeve;
   18) a coil support;
   19) an inductor;
   20) a printed circuit board;
   21) a first end cover;
   22) a first cover plate covering the first end cover;
   23) a button;
   24) a circuit board;
   25) two electrical contacts;
   26) a battery;
   27) a housing;
   28) a second end cover; and
   29) a second cover plate covering the second end cover;
   wherein:
   the thermal insulation cotton is sheathed on the stainless-steel tube;
   the first end support and the second end support are disposed on two ends of the stainless-steel tube, respectively;
   the first lock block is disposed on the first end support;
   the ring comprising stainless iron is in threaded connection to the first lock block, and the eye ring is removably disposed on the ring comprising stainless iron;
   the eye ring, the ring comprising stainless iron, the first lock block, and the first end support and the stainless-steel tube each comprise a central hole, so that a cigarette passes through the central hole of each component to enter the stainless-steel tube;
   the first end support, the stainless-steel tube, and the second end support are disposed sequentially in that order in the support cylinder;
   the magnet is fixed on the second lock block, and the support cylinder is supported by the second lock block;
   the spring is disposed in the spring support; the thermistor is disposed in the mounting seat; the mounting seat is disposed on the spring support; and the spring support is embedded in the support cylinder;
   the pneumatic switch is disposed in the silicone sleeve; the silicone sleeve is disposed in the annular sleeve; the annular sleeve is embedded in the coil support;
   the inductor is disposed on the coil support; the inductor comprises two pins and the printed circuit board is directly connected to the two pins;
   the coil support is disposed in the housing; the support cylinder is disposed in the coil support;
   the battery is disposed in the housing; the button is disposed on the housing; the two electrical contacts are directly connected to the circuit board; the two electrical contacts and the circuit board are disposed in the housing;
   the first cover plate and the first end cover are sequentially disposed on one end of the housing; and
   the second cover plate and the first end cover are sequentially disposed on an other end of the housing.

* * * * *